(12) United States Patent
Baldwin et al.

(10) Patent No.: US 11,278,649 B2
(45) Date of Patent: Mar. 22, 2022

(54) SURFACE COATINGS

(71) Applicant: MicroVention, Inc., Aliso Viejo, CA (US)

(72) Inventors: Aaron Baldwin, Orange, CA (US); John Belletto, Yorba Linda, CA (US); Wendy Beuthin, San Clemente, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 144 days.

(21) Appl. No.: 16/712,582

(22) Filed: Dec. 12, 2019

(65) Prior Publication Data

US 2020/0222594 A1 Jul. 16, 2020

Related U.S. Application Data

(62) Division of application No. 15/724,135, filed on Oct. 3, 2017, now Pat. No. 10,543,299.

(60) Provisional application No. 62/403,562, filed on Oct. 3, 2016.

(51) Int. Cl.
| | |
|---|---|
| *A61L 31/10* | (2006.01) |
| *A61L 31/16* | (2006.01) |
| *A61L 31/06* | (2006.01) |
| *A61F 2/91* | (2013.01) |
| *A61F 2/88* | (2006.01) |
| *A61F 2/82* | (2013.01) |

(52) U.S. Cl.
CPC .............. *A61L 31/10* (2013.01); *A61F 2/885* (2013.01); *A61F 2/91* (2013.01); *A61L 31/06* (2013.01); *A61L 31/16* (2013.01); *A61F 2/82* (2013.01); *A61F 2210/0076* (2013.01); *A61F 2230/0019* (2013.01); *A61F 2240/001* (2013.01); *A61F 2250/0067* (2013.01); *A61L 2300/42* (2013.01); *A61L 2400/18* (2013.01); *A61L 2420/02* (2013.01)

(58) Field of Classification Search
None
See application file for complete search history.

(56) References Cited

U.S. PATENT DOCUMENTS

| | | | |
|---|---|---|---|
| 4,378,430 | A | 3/1983 | Modrovich |
| 4,459,317 | A | 7/1984 | Lambert |
| 4,465,770 | A | 8/1984 | Modrovich |
| 4,487,808 | A | 12/1984 | Lambert |
| 5,077,352 | A | 12/1991 | Elton |
| 5,164,321 | A | 11/1992 | Zdunek et al. |
| 5,225,267 | A | 7/1993 | Ochi et al. |
| 5,281,468 | A | 1/1994 | Klier et al. |
| 5,545,208 | A | 8/1996 | Wolff et al. |
| 5,662,960 | A | 9/1997 | Hostettler et al. |
| 5,753,453 | A | 5/1998 | Kwan |
| 5,776,661 | A | 7/1998 | Casaletto |
| 5,804,299 | A | 9/1998 | Nakata et al. |

(Continued)

OTHER PUBLICATIONS

International Search Report and Written Opinion for International Application No. PCT/US2013/028380 filed on Feb. 28, 2013.

(Continued)

*Primary Examiner* — Aradhana Sasan

(74) *Attorney, Agent, or Firm* — K&L Gates LLP; Brian J. Novak; Benjamin D. Heuberger

(57) ABSTRACT

Described herein are substrate coatings.

19 Claims, 4 Drawing Sheets

(56) References Cited

U.S. PATENT DOCUMENTS

| | | | |
|---|---|---|---|
| 5,888,656 | A | 3/1999 | Suzuki et al. |
| 6,030,656 | A | 2/2000 | Hostettler et al. |
| 6,083,257 | A | 7/2000 | Taylor |
| 6,099,562 | A | 8/2000 | Ding |
| 6,673,453 | B2 | 1/2004 | Beavers |
| 6,803,069 | B2 | 10/2004 | Patnaik et al. |
| 7,008,979 | B2 | 3/2006 | Schottman |
| 7,264,859 | B2 | 9/2007 | Rouns |
| 7,494,687 | B2 | 2/2009 | Cox |
| 7,544,381 | B2 | 6/2009 | Kangas |
| 7,544,673 | B2 | 6/2009 | DeWitt |
| 7,553,546 | B1 | 6/2009 | Tan |
| 7,770,828 | B2 | 8/2010 | Matsumoto et al. |
| 2002/0082679 | A1 | 6/2002 | Sirhan |
| 2002/0120033 | A1 | 8/2002 | Keogh et al. |
| 2003/0069647 | A1 | 4/2003 | Desmond |
| 2003/0187493 | A1 | 10/2003 | Campbell et al. |
| 2006/0052757 | A1* | 3/2006 | Fischer, Jr. ........ A61M 25/0045 604/265 |
| 2009/0076596 | A1 | 3/2009 | Adden et al. |
| 2009/0112239 | A1 | 4/2009 | To |
| 2009/0297607 | A1* | 12/2009 | Wang .................... A61K 47/34 424/486 |
| 2010/0105799 | A1 | 4/2010 | Rudd |
| 2010/0236684 | A1 | 9/2010 | Garlough |
| 2011/0000788 | A1 | 1/2011 | Deschamps |
| 2011/0117282 | A1 | 5/2011 | Bernard |
| 2011/0160382 | A1* | 6/2011 | Pacetti .................... A61P 29/00 524/516 |
| 2013/0243936 | A1 | 9/2013 | Garretson et al. |
| 2018/0093019 | A1 | 4/2018 | Baldwin et al. |

OTHER PUBLICATIONS

Bruice, Acid-Base Properties of Amino Acids. Organic Chemistry, Fifth Edition (textbook), Pearson Education Inc., p. 1025 (2007).

Weber, Use of ionic and zwitterionic (Tris/BisTris and HEPES) buffers in studies on hemoglobin function. J Appl. Physiol., 72(4):1611-1615 (1992).

Tsai et al., Dopamine-assisted immobilzation of poly(ethylene imine) based polymers for control of cell-surface interactions. Acta Biomaterialia 7, pp. 2518-2525 (2011).

* cited by examiner

SURFACE COATINGS

CROSS REFERENCE TO RELATED APPLICATIONS

This application is a divisional of U.S. patent application Ser. No. 15/724,135, filed Oct. 3, 2017, which claims the benefit of U.S. provisional patent application No. 62/403,562, filed Oct. 3, 2016, the entire disclosure of which is incorporated herein by reference.

SUMMARY

Described herein are substrate coatings. In some embodiments, the substrates can be associated with a medical device such as an implantable medical device. Implantable medical devices can include, but are not limited to flat coupons, hypo tubes, wires, woven wires, and/or laser cut objects. In one embodiment, an implantable medical device can be a stent.

In some embodiments, coatings can include polydopamine and polyethyleneimine and an increase positive charge on a surface. In other embodiments, coatings can include polycatechol. In some embodiments, the polycatechol can increase positive charge on a surface. In other embodiments, the polycatechol can increase negative charge on a surface.

Methods are also described for forming the herein described coatings. In one embodiment, a method can functionalize a surface, such as an implantable medical device surface. The method can include depositing a dopamine or dopamine-like compound on the surface. In some embodiments, the method can further include conjugating phosphate containing compounds onto the surface.

In some embodiments, the coatings described herein can be phosphorylcholine coatings.

DETAILED DESCRIPTION

Described herein are substrate coatings. The coatings can be used for implantable medical devices.

Implant thrombogenicity continues to be a key issue in the treatment of neurovascular aneurysms especially with coil assist and flow diversion stents. In general, any foreign implanted material in the parent aneurysmal vessel has a risk of causing thrombosis formation. One way to reduce this risk is to impart a biocompatible surface on the implanted device by coating or chemically functionalizing the implant. Coating a braided nitinol stent such as LVIS® (Intraluminal Support Device, MicroVention, Inc., Tustin, Calif.) or FRED® (Flow Re-Direction Endoluminal Device, MicroVention, Inc., Tustin, Calif.) is not permitted due to the movement of each wire when the stent is collapsed, thus surface functionalization without locking the wires is necessary.

Figure 1:
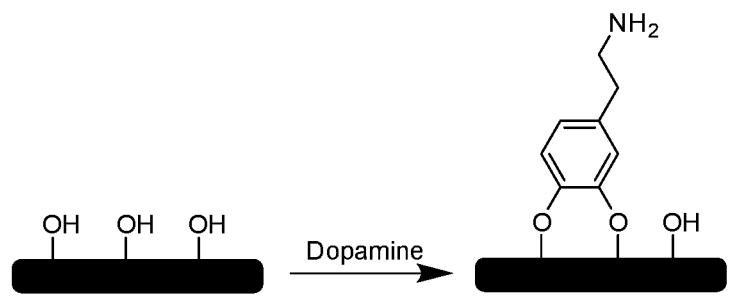
FIG. 1 shows one suggested pathway dopamine may react with hydroxyl surface functionality.

In one embodiment, surface modification of nitinol is described. One method of surface functionalizing nitinol is through silane chemistry. One possible chemical reactivity scheme that has high adherence to many materials is dopamine. Dopamine was elucidated by analysis of the adhesive proteins secreted by mussels for attachment to surfaces. FIG. 1 indicates one suggested pathway the dopamine may react with hydroxyl surface functionality. This representation may be largely simplified. However, when using dopamine, the actual substrate may not need to have hydroxyl functionality. The reaction process can yield very complicated structures and is in part the reason why many different types of materials can be functionalized with dopamine.

In some embodiments, dopamine can be used to act as a tie layer to further react biocompatible molecules or polymers to an implantable medical device. In some embodiments, the implantable medical device can be a woven stent platform.

Dopamine is a small molecule which autopolymerizes in aqueous solutions in the presence of oxygen and basic pH (pH>7). This polymerization occurs from the catechol structure of the dopamine molecule. In some embodiments, amine functionality on the dopamine molecule can provide a possibility for modification post polymerization. Furthermore, the dopamine autopolymerization can proceed in a simplistic and robust reaction system compared with other catechols or other types of surface functionalization methods.

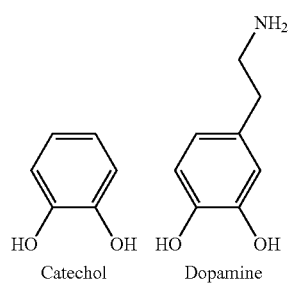

In some embodiments, dopamine-like compounds can be used. These compounds can have similar deposition characteristics. In one embodiment, a dopamine-like compound can be L-Dopa (L-3,4-dihydroxyphenylalanine).

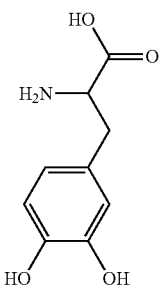

L-Dopa (L-3,4-dihydroxyphenylalanine)

This molecule autopolymerizes in a similar manner to dopamine. In some embodiments, L-Dopa may need a salt to screen the carboxylic acid charge for successful polymerization. L-Dopa is a molecule which polymerizes in high pH aqueous media with exposure to dissolved oxygen or other oxidizing agent (e.g., ammonium persulfate, sodium periodate, copper sulfate). Another dopamine-like compound is 3,4-dihydroxyphenylacetic acid.

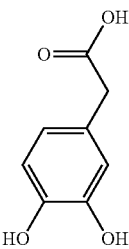

3,4-Dihydroxyphenylacetic acid

Non-functional catechol can autopolymerize and be deposited in aqueous solutions similar to dopamine. However, additional components may be required to allow for post autopolymerization functionalization. In some embodiments, a multifunctional polyamine, branched polyethyleneimine can be used to add amine functionality for later reactions. Other embodiments can include difunctional amines such as ethylenediamine, propylenediamine, or multifunctional polyelectrolytes such as polyallylamine. Adding a multifunctional amine can enable the polymerization and deposition of the catechol as well as providing amines for post deposition processing.

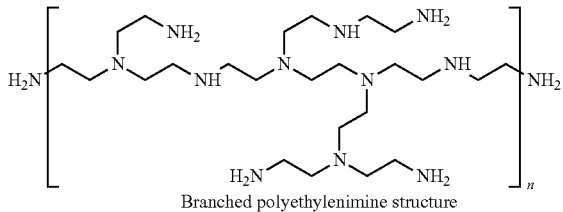

Branched polyethylenimine structure

In some embodiments, branched polyethylenimine can be used in the catechol reaction process. In some embodiments, a Tris buffer can be used in the reaction of dopamaine (FIG. 2), whereby the addition of Tris to a ring occurs from a Michael addition and/or Schiff base reaction.

In other embodiments, other amine functional materials can be utilized to impart additional functionality to dopamine and other catechol reaction systems. Other amine functional materials can include phosphorylethanolamine and taurine.

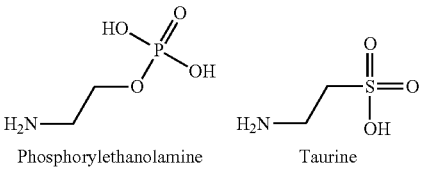 [SMILES: NCCOP(=O)(O)O ; NCCS(=O)(=O)O]

Phosphorylethanolamine      Taurine

Figure 2:
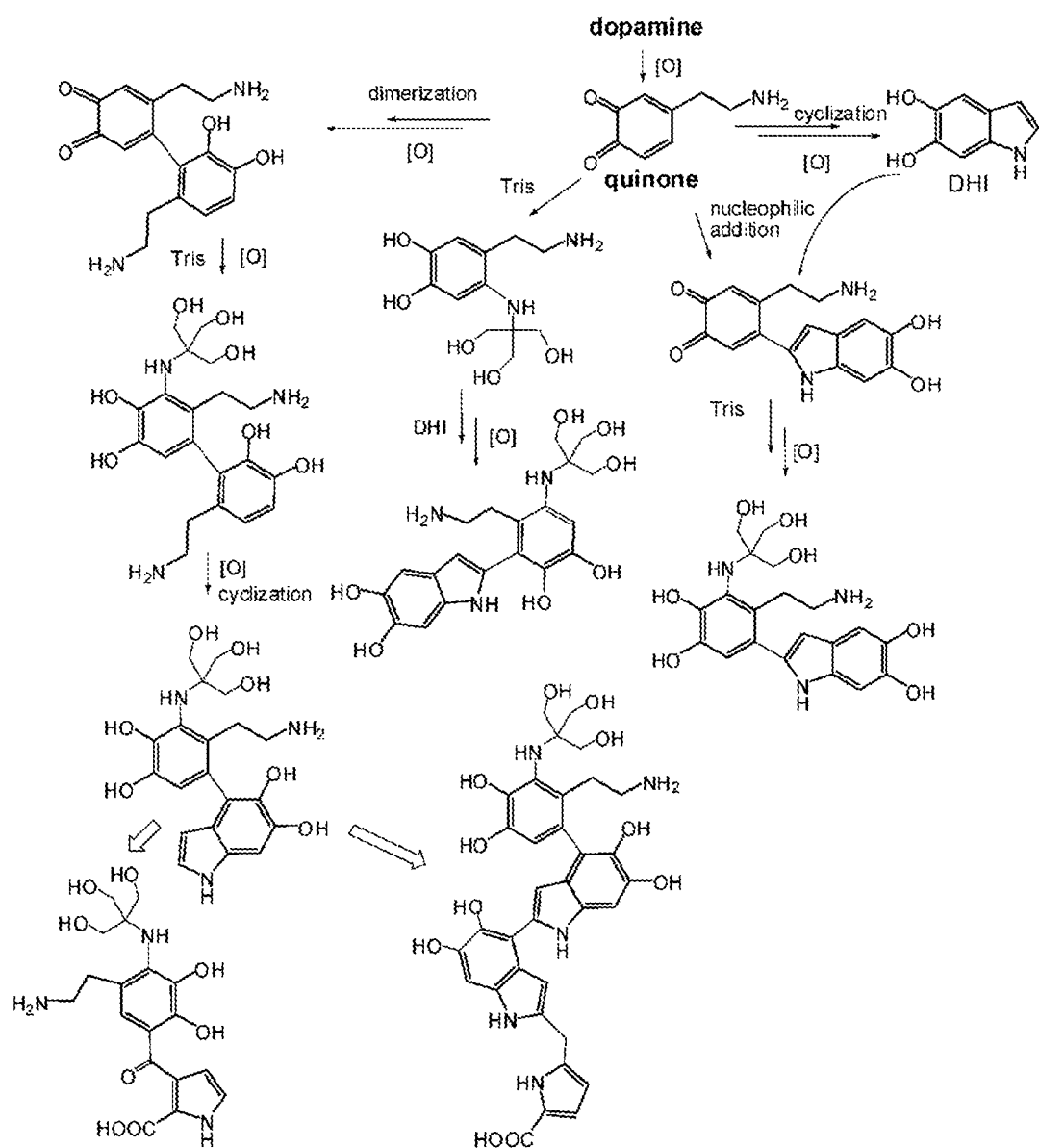
FIG. 2 shows dopamine polymerization with reaction of Tris buffer.

These molecules can react during polymerization with catechols similarly to Tris buffer as demonstrated in FIG. 2. Adding these functional molecules during the polymerization of the catechol can provide at least two benefits. First, these molecules are charged at physiological pH and thus may add hydrophilicity to the polycatechol coating. Secondly, the functional molecule can be added concomitantly with the polymerization, therefore, a secondary reaction may not be necessary.

In some embodiments, catechol/amine technology is described as a standalone coating method for vessel occluding devices, whereby the increased amine content can act as a biological binding agent to decrease the time to occlusion for vessel occluding devices.

Positively charged surfaces on implanted materials can cause benefits and detractions for medical devices. In some embodiments, positive charged polyallylamine coatings on stainless steel can increase platelet adherence, platelet activation, and fibrinogen adsorption. These interactions can then be quenched by subsequent modification of the polyallylamine coating. In some embodiments, the interactions can be quenched with heparin. These platelet and fibrinogen type reactions can be deleterious for stent applications where vessel patency is a necessity. However, these characteristics can be used for vessel occlusion. In one embodiment, a vessel occluding devices may be coated with polydopamine and PEI to increase the content of positive charged amines on the surface.

Other embodiments provide for the attachment of phosphate containing compounds to any substrate that has been functionalized with dopamine, (poly)dopamine, and/or silane chemistry. Phosphorylcholine contains a phosphate group and can be directly reacted to an amine functionalized substrate. Other phosphate containing molecules can also be reacted to the dopamine, (poly)dopamine, and/or silane functionalized substrate then used as an intermediate to synthesize phosphorylcholine.

A substrate's material composition can be any metallic/alloy (to include but is not limited to nitinol, stainless steel, cobalt chromium), any plastic/polymer (to include but is not limited to grilamide, Pbax, PEEK), or any glass surfaces.

The substrates can be in virtually any form. In one embodiment, the substrate is formed into an implantable medical device. In other embodiments, the substrates may be in the form of a flat coupon, hypo tube, wire, woven wire, or laser cut object. In one embodiment, the substrate may be formed into a stent such as a braided stent platform.

In some embodiments, the phosphate containing compound can be any compound containing a phosphate or cyclic phosphate group. These compounds can include, but are not limited to phosphorylcholine and 2-chloro-2-oxo-1,3,2-dioxaphospholane.

In other embodiments, carbodiimide molecules can be any carbodiimide including, but is not limited to 1-ethyl-3-(3-dimethylamineopropyl) carbodiimide (EDC).

Figure 3:
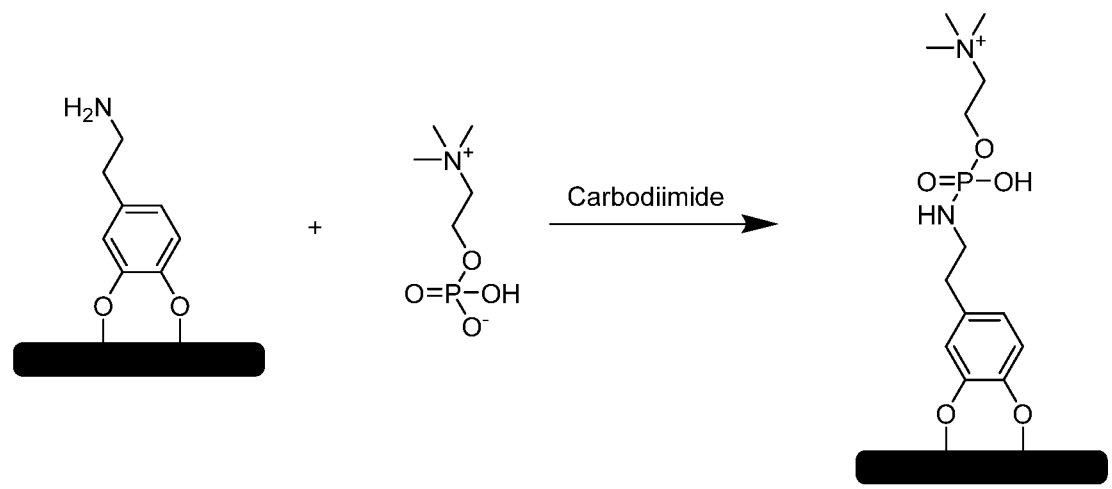
FIG. 3 shows a reaction for applying a phosphorylcholine coating to a (poly)dopamine functionalized substrate.

In some embodiments, molecules containing phosphate groups may be conjugated to amine-containing molecules via a carbodiimide reaction. The carbodiimide can activate the phosphate to an intermediate phosphate ester. In the presence of an amine, the ester can react to form a stable phosphoramidate bond. Such a reaction scheme can be to immerse the amine functionalized material in a phosphorylcholine solution (i.e. water, saline, buffer solution or any applicable organic solvent) containing EDC. Substrate can be incubated in the reaction mixture. Upon completion, any non-reacted started materials can be removed by a series of washing steps and drying. See FIG. 3 and FIG. 4.

Figure 5:
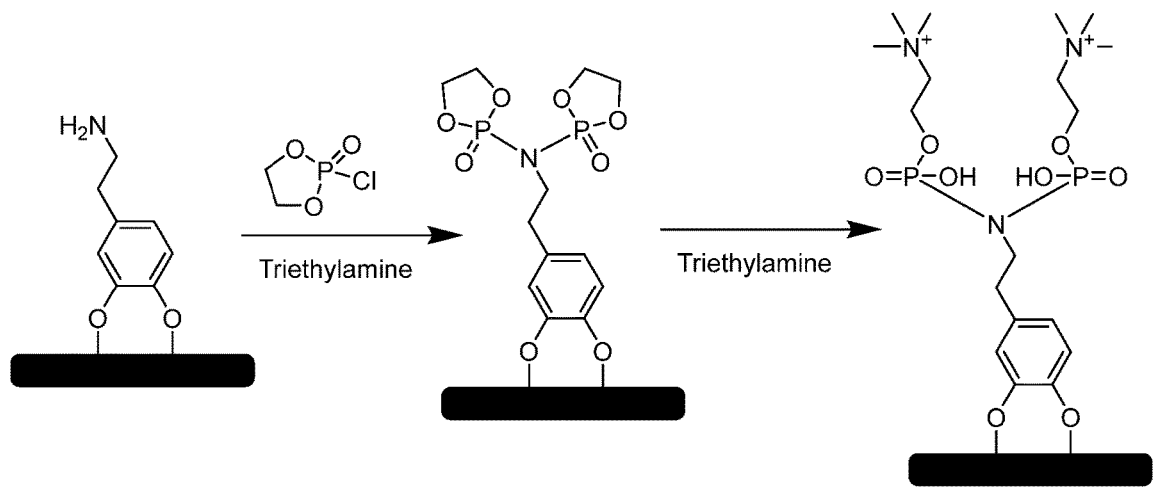
FIG. 5 shows a reaction for synthesizing a phosphorylcholine coating to a (poly)dopamine functionalized substrate.
Figure 6:
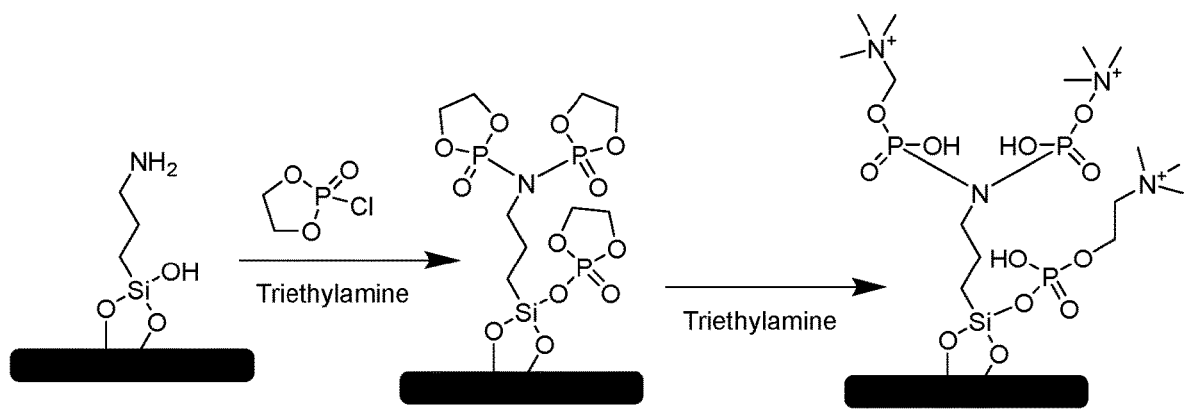
FIG. 6 shows a reaction for synthesizing a phosphorylcholine coating to a silane functionalized substrate.

In another embodiment, 2-chloro-2-oxo-1,3,2-dioxaphospholane (COP) can be reacted with available amines in the presence of TEA to form a substrate/COP intermediate. The intermediate structure can further be treated with trimethylamine to synthesize a phosphorylcholine rich surface. Any unreactive materials can be removed by a series of washing steps. See FIG. 5 and FIG. 6.

In some embodiments, the above listed technologies can be used as a tie layer for subsequent functionalizing an implantable medical device with phosphorylcholine (polydopamine, polydopamine w/polyethylenimine, L-Dopa) or as a one-step coating (dopamine, L-Dopa, or catechol combined w/phosphorylethanolamine or taurine). In one embodiment, the technologies can be used to passivate the surface of a MicroVention FRED® device.

In one embodiment, a reaction scheme can be to immerse the completed assembled woven stent in a water or buffer (Tris, Bicine, Phosphate, etc.) solution containing dopamine (1 mg/ml) at a pH of 7.5-10.5. The reaction can be protected from UV light and done at room temperature to 60° C. for 1 to 24 hrs. The resulting woven stents can then be rinsed with copious amounts of water and dried in a vacuum oven or inert gas oven at elevated temperature or room temp.

Figure 4:
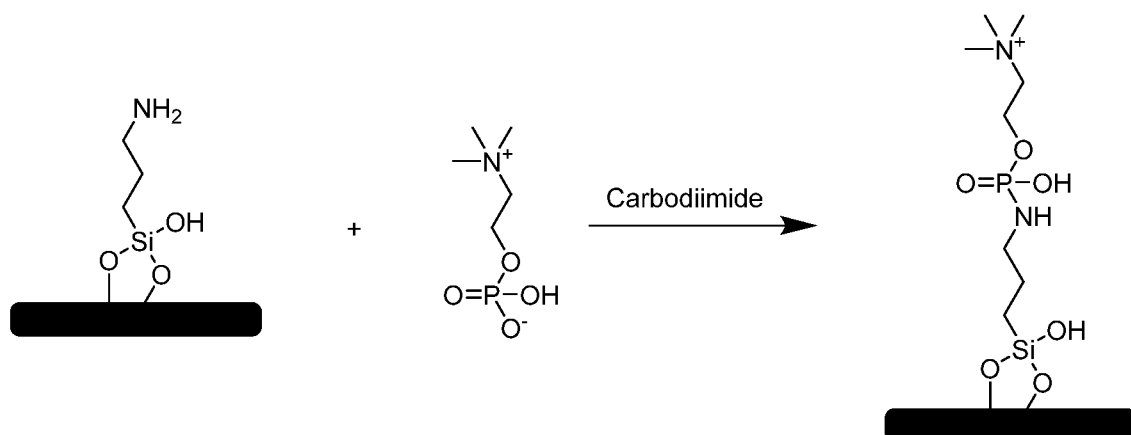
FIG. 4 shows a reaction for applying a phosphorylcholine coating to a silane functionalized substrate.
Figure 7:
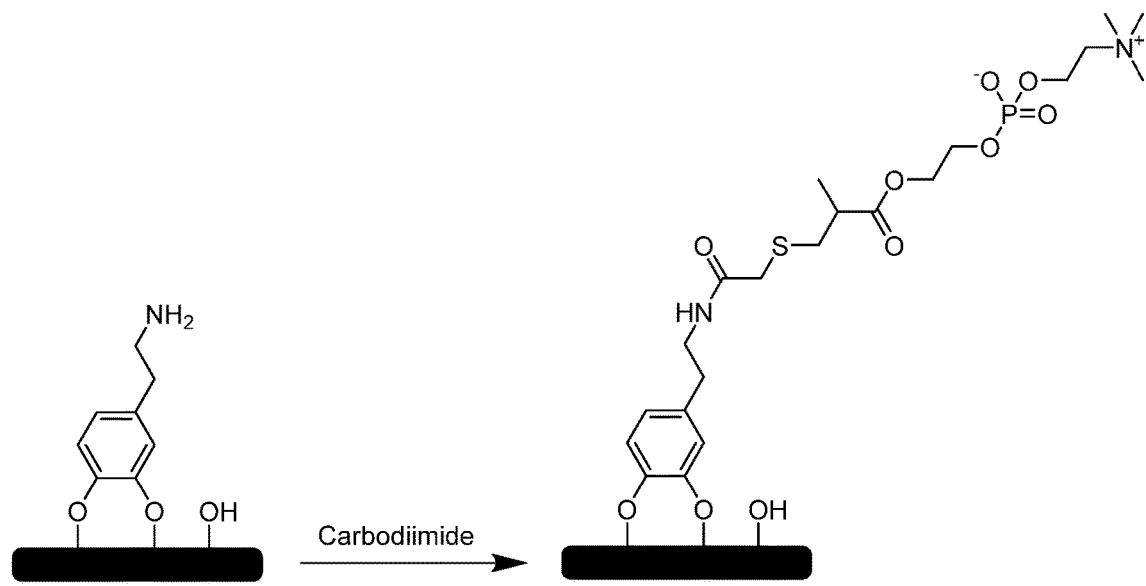
FIG. 7 shows carbodiimide coupling of carboxylic acid functionalized phosphorylcholine (NOF Lipidure-RC01) to free amines of dopamine.
Figure 8:
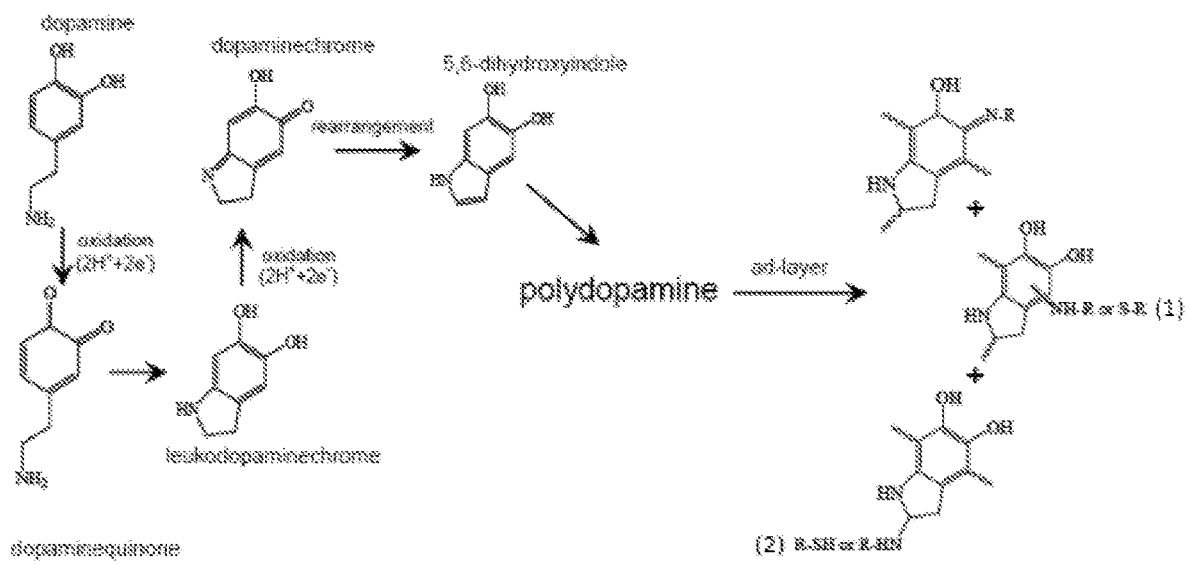
FIG. 8 shows that the dopamine coating process can eventually lead to a polydopamine coating with a mixture of dopamine derivatives as shown, some of which are amendable to Schiff-base addition (1) or Michael addition (2).

The resulting coated stent can then be amendable to three types of further surface modification: carbodiimide condensation of dopamine free amines with carboxylic acid (FIG. 7), reaction with thiols or amines through Michael addition, or Schiff base formation (FIG. 8). FIG. 7 displays a carbodiimide coupling of a phosphorylcholine molecule (NOF Lipidure-RC01), a cell wall mimic that has shown to greatly improve the biocompatibility of stents and other implant devices. FIG. 4 displays a few of the intermediate chemical species present during an initial deposition of dopamine. Some of the final structures may be reactive to thiol or amine functional materials such as polymers, macromers and small molecules.

Dopamine coatings may be insensitive to substrate type and/or robust with regards to high adhesion. This surface functionalization can also have the flexibility of accepting many different secondary reactions in which a biocompatible functionality may be imparted through reactions with small molecules, macromers, or polymers.

In some embodiments, an amine rich coating as described herein may induce a faster occlusion time when compared with a non-coated device. The occlusion time can be increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, between about 5% to about 35%, or between about 35% to about 65%, when compared to a non-coated device.

In other embodiments, the surface composition/coating can include an increase in atomic nitrogen concentration of about 4% in the treated state when compared to an untreated surface. In some embodiments, the increase in the atomic nitrogen concentration can be about 0.5%, about 1%, about 2%, about 4%, about 5%, about 6%, about 7%, about 8%, about 9%, about 10%, about 20%, about 30%, about 40%, about 50%, more than 50%, between about 0.5% to about 4.5%, or between about 1% to about 10% in the treated state when compared with the untreated surface.

In some embodiments, the treated surfaces of the devices can delay peak thrombin generation time. In some embodiments, the treated surfaces can delay the peak thrombin generation time by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, between about 5% to about 35%, between about 35% to about 65%, between about 65% to about 100% when compared to an untreated surface of a device.

In other embodiments, the treated surfaces of the devices can decrease the peak thrombin concentration at the treated surface when compared to an untreated surface. In some embodiments, the treated surfaces can decrease the peak thrombin concentration by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, between about 5% to about 35%, between about 35% to about 65%, between about 65% to about 100% when compared to an untreated surface.

Example 1

Electropolished nitinol test coupons were initially coated to investigate the amount of amine deposited on the surface with polydopamine/PEI and polydopamine/tris(hydroxymethyl)aminomethane (TRIS)/PEI solutions. Reaction buffers were dissolved as listed in Table I. Samples were incubated for 4 hrs at room temperature. The coating composition was determined with x-ray photoelectron spectroscopy (XPS) (Table II). XPS determines the atomic concentration for the top 10 nm of material. Therefore, a thicker coating will completely block the signal from titanium and nickel. The polydopamine/PEI-high had the highest nitrogen to carbon ratio, an indicator that the coating, although thinner than the others, would have the highest surface charge compared to the other reactions. Thus, polydopamine/PEI-high reaction conditions were chosen to coat occluder devices, but increasing the reaction time to 16-18 hrs to create a thicker coating.

TABLE I

Nitinol coupon deposition solution conditions

| Sample | PEI (mM) | TRIS (mM) | Dopamine (mM) |
| --- | --- | --- | --- |
| Polydopamine/PEI-Low | 4.1 mM | — | 21.1 |
| Polydopamine/PEI-High | 20 mM | — | |
| Polydopamine/TRIS/PEI | 4.1 mM | 10 mM | |

TABLE II

XPS results in atomic concentrations (Atomic %)

| Sample | C | N | O | Na | Si | S | Cl | Ca | Ti | Ni |
|---|---|---|---|---|---|---|---|---|---|---|
| Polydopamine/PEI-Low | 59.0 | 15.3 | 21.4 | 1.4 | — | — | 0.4 | — | 1.9 | 0.6 |
| Polydopamine/PEI-High | 33.7 | 10.3 | 37.9 | 0.2 | — | — | 0.2 | — | 14.0 | 3.7 |
| Polydopamine/TRIS/PEI | 64.1 | 16.6 | 17.9 | — | 0.5 | 0.2 | 0.1 | — | 0.5 | 0.3 |

Vessel occluder devices were composed of a braided Nitinol wire basket with an expanded PTFE membrane covering the cross-section of the device.

The devices were coated with a polydopamine/PEI-High solution as listed in Table I, incubating overnight for 16-18 hrs on a rocker at room temperature. The coated devices were then loaded and used as normal.

An 8 mm occluder was implanted in a 5.3 mm branch of the R. Subclavian artery of a swine. The device occluded the vessel abruptly after being implanted for 3 minutes. The average occlusion time for 6 non-coated devices was approximately 7 minutes. These initial results indicate the positive amine rich coating may induce a faster occlusion time when compared with an uncoated device.

Example 2

Polycatechol Functionalized Nitinol Coupons for Subsequent Phosphorylcholine Polymer Attachment Electropolished and nitric acid passivated test coupons were coated with an L-Dopa/Bicine solution. Briefly, a 2 mg/mL L-Dopamine solution was dissolved in a bicine buffer (10 mM Bicine, 0.25 M NaCL, pH 8.5). The nitric acid passivated coupons were agitated in the L-dopamine solution for 18 hrs. Dried samples were then incubated for 18 hrs in a 0.1 M 2-(N-morpholino)ethanesulfonic acid buffer containing 0.7 wt % amine functional phosphorylcholine polymer (Lipidure-NH01, NOF) and 1.0% 1-Ethyl-3-(3-dimethylaminopropyl)carbodiimide.

The surface composition was determined using XPS Table III. The presence of a phosphorylcholine polymer is indicated by the increase in concentration of phosphorus on the surface, and decrease in the base material nickel and titanium percentages.

TABLE III

XPS results in atomic concentrations (Atomic %)

| | C | N | O | Na | Si | P | S | Cl | K | Ca | Ti | Ni |
|---|---|---|---|---|---|---|---|---|---|---|---|---|
| Untreated | 19.8 | 1.3 | 52.1 | — | 0.3 | — | 0.5 | — | — | — | 21.2 | 4.9 |
| Treated | 34.8 | 5.5 | 43.1 | 4.4 | 0.7 | 1.8 | 0.6 | 0.4 | 0.8 | 0.2 | 6.2 | 1.7 |

Phosphorylcholine coatings are known to increase the blood compatibility of medical devices. To this end, the treated samples were tested using a thrombin generation assay (Thrombinoscope, Diagnostica Stago) using a modified thrombogram test method. Briefly, 300 μL of platelet poor citrated human plasma was added to each well of a 96 well plate. Test coupons were loaded into individual wells. Calibration wells were used to determine the concentration of thrombin generated. Time to peak (ttPeak) thrombin generation and peak thrombin generation can be seen in Table IV. The treated surfaces delayed the peak thrombin generation time and decreased the peak thrombin concentration to near that of a blank well indicating the treated samples may have increased blood compatibility.

TABLE IV

Thrombogram results for coated nitinol materials

| | Peak (nM) | ttPeak (min) |
|---|---|---|
| Untreated | 597 ± 74 | 9.5 ± 0.4 |
| Treated | 216 ± 61 | 23.7 ± 3.9 |
| Blank Well | 187 ± 22 | 29.6 ± 3.1 |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An implantable device, including a surface having a coating, wherein the coating includes:
    a polydopamine coating deposited on the surface, wherein the polydopamine coating is formed from at least one dopamine or dopamine-like compound; and
    a coating deposited on the polydopamine coating, wherein the coating deposited on the polydopamine coating is formed from at least one primary amine zwitterion.

2. The implantable device of claim 1, wherein the dopamine or dopamine-like compound increases positive charge on the implantable device.

3. The implantable device of claim 1, wherein the dopamine or dopamine-like compound increases negative charge on the implantable device.

4. The implantable device of claim 1, wherein the coating induces a faster occlusion time when compared to a non-coated device.

5. The implantable device of claim 1, wherein the implantable device is a flat coupon, a hypo tube, a wire, a woven wire, a stent, or a laser cut object.

6. The implantable device of claim 1, wherein the implantable device is a stent.

7. The implantable device of claim 1, wherein the coating further includes a diamine, multifunctional amine, or multifunctional amine polymer.

8. The implantable device of claim 1, wherein the at least one primary amine zwitterion includes a phosphate-containing primary amine zwitterion.

9. The implantable device of claim 1, wherein the at least one dopamine or dopamine-like compound includes

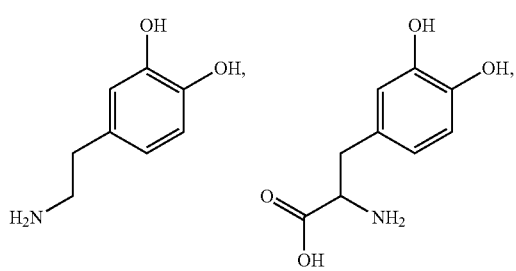

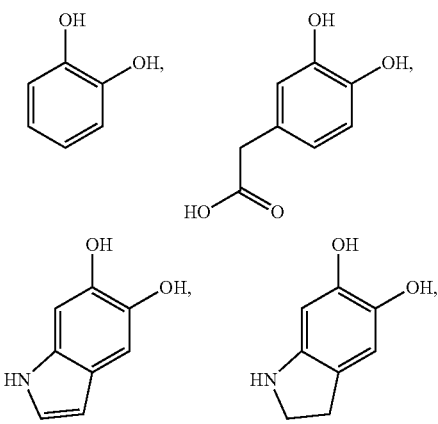

or a combination thereof.

10. The implantable device of claim 1, wherein the at least one primary amine zwitterion includes phosphorylethanolamine.

11. The implantable device of claim 1, wherein the at least one primary amine zwitterion includes taurine.

12. The implantable device of claim 1, wherein the coating deposited on the polydopamine coating includes

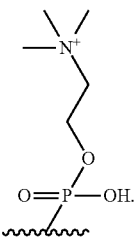 [SMILES: *P(=O)(O)OCC[N+](C)(C)C]

13. The implantable device of claim 1, wherein the coating deposited on the polydopamine coating includes

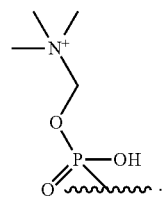 [SMILES: *P(=O)(O)OC[N+](C)(C)C]

14. The implantable device of claim 1, wherein the coating deposited on the polydopamine coating includes

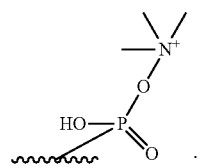 [SMILES: *P(=O)(O)O[N+](C)(C)C]

15. The implantable device of claim 1, wherein the coating includes

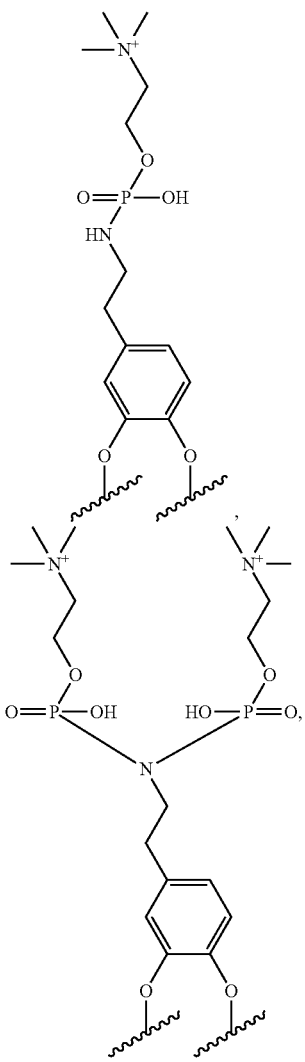
,

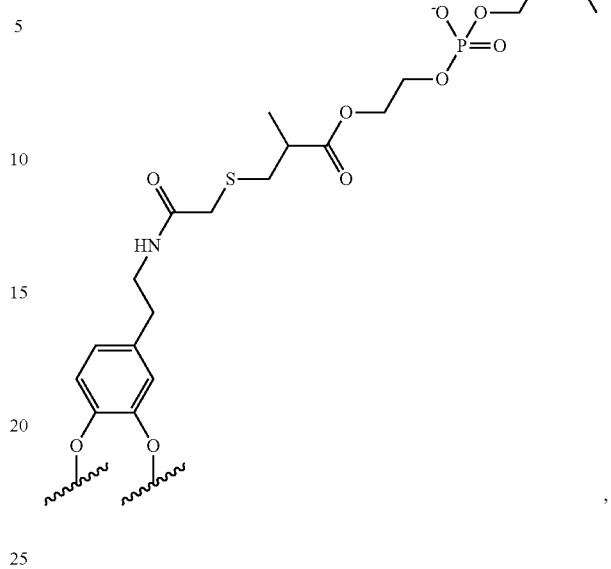
, or a combination thereof.

16. The implantable device of claim 1, wherein the coating includes a phosphoramidate.

17. The implantable device of claim 1, wherein the coating deposited on the polydopamine coating includes a phosphorylcholine polymer.

18. The implantable device of claim 1, wherein the polydopamine coating is covalently deposited on the surface.

19. The implantable device of claim 1, wherein the coating deposited on the polydopamine coating is covalently deposited on the polydopamine coating.

* * * * *